US009200885B2

(12) United States Patent
Ressler et al.

(10) Patent No.: US 9,200,885 B2
(45) Date of Patent: Dec. 1, 2015

(54) INTERFEROMETER HAVING MULTIPLE SCAN CARRIAGES

(71) Applicant: AGILENT TECHNOLOGIES, INC., Loveland, CO (US)

(72) Inventors: Gregg Ressler, Shelton, CT (US); Jeffrey H. Saller, Milford, CT (US)

(73) Assignee: Agilent Technologies, Inc., Santa Clara, CA (US)

(*) Notice: Subject to any disclaimer, the term of this patent is extended or adjusted under 35 U.S.C. 154(b) by 0 days.

(21) Appl. No.: 14/561,425

(22) Filed: Dec. 5, 2014

(65) Prior Publication Data
US 2015/0083916 A1    Mar. 26, 2015

Related U.S. Application Data

(63) Continuation of application No. 13/723,274, filed on Dec. 21, 2012, now Pat. No. 8,933,406.

(51) Int. Cl.
| | |
|---|---|
| *G01B 9/02* | (2006.01) |
| *G01N 21/35* | (2014.01) |
| *G01J 3/06* | (2006.01) |
| *G01J 3/453* | (2006.01) |
| *G02B 7/182* | (2006.01) |
| *G01J 3/45* | (2006.01) |

(52) U.S. Cl.
CPC .............. *G01B 9/02* (2013.01); *G01B 9/02015* (2013.01); *G01J 3/06* (2013.01); *G01J 3/45* (2013.01); *G01J 3/4535* (2013.01); *G01N 21/35* (2013.01); *G02B 7/182* (2013.01); *G01J 2003/061* (2013.01); *G01N 2021/3595* (2013.01); *G01N 2201/061* (2013.01); *G01N 2201/10* (2013.01)

(58) Field of Classification Search
CPC .............................. G01B 9/02015; G01B 9/02
See application file for complete search history.

(56) References Cited

U.S. PATENT DOCUMENTS

| | | | |
|---|---|---|---|
| 4,693,603 | A | 9/1987 | Auth |
| 5,486,917 | A | 1/1996 | Carangelo et al. |
| 6,836,968 | B1 | 1/2005 | Walker et al. |
| 7,630,081 | B2 | 12/2009 | Ressler et al. |

(Continued)

OTHER PUBLICATIONS

David W. Walser et al., "Double-Parallelogram Carriage for Spectrometer Mirrors," NASA Tech Briefs, www.techbriefs.com/index.php?option=com_staticxt&staticfile=/Briefs/Aug01/GSC14297.html, pp. 1-2.

(Continued)

*Primary Examiner* — David Porta
*Assistant Examiner* — Hugh H Maupin

(57) ABSTRACT

An interferometer includes a first assembly having a base, a beam splitter assembly to split light into first and second portions, and a fixed mirror for reflecting the first portion of light; and a second assembly movable with respect to the first assembly, and having first and second scan carriages, and a movable mirror connected to the second scan carriage for reflecting the second portion of light. The beam splitter assembly combines the reflected first and second portions of light into a recombined radiation beam. Inner bearing flexures enable movement of the first scan carriage relative to the base, and outer bearing flexures enable movement of the second scan carriage relative to the first scan carriage, such that a plane containing the movable mirror is maintained parallel to multiple planes containing the movable mirror at respective distances between the second and first assemblies during scan movement of the movable mirror.

20 Claims, 8 Drawing Sheets

(56) References Cited

U.S. PATENT DOCUMENTS

| | | |
|---|---|---|
| 8,205,853 B2 | 6/2012 | Bleier et al. |
| 2008/0170231 A1 | 7/2008 | Ressler et al. |
| 2008/0285044 A1 | 11/2008 | Sin et al. |
| 2010/0012808 A1 | 1/2010 | Jacobson et al. |
| 2012/0120404 A1 | 5/2012 | Coffin |

OTHER PUBLICATIONS

P.R. Lawson et al., "Cryogenic Delay Line for Long-Baseline Interferometry in the Far-Infrared," Second Workshop on New Concepts for Far-Infrared and Submillimeter Space Astronomy, pp. 408-414.

UK Search Report dated Apr. 3, 2014.

INTERFEROMETER HAVING MULTIPLE SCAN CARRIAGES

CROSS-REFERENCE TO RELATED APPLICATIONS

This application is a continuation application under 37 C.F.R. §1.53(b) of U.S. patent application Ser. No. 13/723,274, filed on Dec. 21, 2012, in the United States Patent and Trademark Office. Priority under 35 U.S.C. §120 is claimed from U.S. patent application Ser. No. 13/723,274, the entire disclosure of which is specifically hereby incorporated by reference.

BACKGROUND

Michelson interferometers are used in many commercial applications. Performance characteristics and stability limitations of various designs are well known and understood. Slight misalignments of optical elements in a conventional interferometer cause modulation changes that may significantly affect the performance of the interferometer. There have been numerous attempts in the design of commercial interferometers, Michelson interferometers included, to reduce misalignments and/or the effects of misalignments. Some of these attempts include passive means, such as using cube corner mirrors, retro-mirrors, and/or other means to compensate for undesirable effects. Other attempts have used active means such as dynamic mirror alignment or active thermal control, among others. Alternatively, adjustment mechanisms are available to enable periodic or necessary reestablishment of the relationships of the optical elements to maintain acceptable alignment conditions.

Generally, Michelson interferometers produce an alternating optical signal by splitting an input beam of light into two portions, inducing an alternating path difference in one of the portions, and recombining the portions at the exact point of initial splitting. Maintaining flatness and consistent geometric relationship (to a wave front) of the mirror element that produces the path difference during a scan (e.g., movable mirror) is important to system performance, stability and ultimately instrument data quality. Any short or long term change (commonly referred to as optical instability) in the geometric relationship or flatness of either the fixed or movable mirrors to the wave front may produce compromised results. Similar results occur when the beam splitter changes flatness or angle relative to the wave front.

Spectral resolution of an interferometer is related to the distance the movable mirror moves during the scan. In the field of Fourier transform infrared (FTIR) spectroscopy instrument design, in particular, movement of the movable mirror is typically achieved via a mechanical bearing. There are many bearing implementations having a wide spectrum of costs and complexity.

Flat springs (bearings or bearing flexures) have been used with interferometers. U.S. Pat. No. 7,630,081, to Ressler et al. (Dec. 8, 2009), which is hereby incorporated by reference, is an example of conventional interferometers. U.S. Pat. No. 7,630,081 addresses use of a pair of bearing flexures, including disclosure of material selection and geometry, to achieve a high degree of performance and thermal/mechanical stability at a relatively low cost and relatively small size. However, such conventional interferometers may have limited resolution capability due to inherent bearing travel restrictions.

Thus, there is a need for high performance, reliable interferometers that are capable of longer bearing travel providing greater resolution, e.g., for mid-level laboratory markets.

SUMMARY

According to a representative embodiment, an interferometer includes a fixed assembly and a movable assembly which is movable with respect to the fixed assembly, a pair of inner bearing flexures and a pair of outer bearing flexures. The fixed assembly includes a base, a beam splitter assembly configured to split light emitted from a light source into first and second portions of light, and a fixed mirror for reflecting the first portion of light. The movable assembly includes an upper scan carriage, a lower scan carriage and a movable mirror connected to the lower scan carriage for reflecting the second portion of light. The beam splitter assembly is further configured to combine the reflected first and second portions of light into a recombined radiation beam. The pair of inner bearing flexures has ends connected to the base and ends connected to the upper scan carriage, enabling movement of the upper scan carriage relative to the base. The pair of outer bearing flexures has ends connected to the upper scan carriage and ends connected to the lower scan carriage, enabling movement of the lower scan carriage relative to the upper scan carriage. The movement of the upper scan carriage and the movement of the lower scan carriage enable a scan movement of the movable mirror in a scan direction restricted such that the scan movement maintains a plane containing the movable mirror parallel to planes containing the movable mirror at respective distances between the movable assembly and the fixed assembly during the scan movement. The beam splitter assembly, the fixed mirror and the movable mirror are positioned within a space between the planes containing the pair of inner bearing flexures while in respective flat conditions.

According to another representative embodiment, a Fourier transform infrared spectroscopy system includes a light source configured to emit infrared radiation, and an interferometer configured to receive the infrared radiation and to provide recombined radiation comprising first and second portions of reflected radiation having varying relative phases. The interferometer includes a beam splitter assembly, a fixed mirror, a movable mirror, upper and lower scan carriages, and a detection system for receiving the recombined radiation. The beam splitter assembly is mounted to a stationary base and configured to split the infrared radiation emitted from the light source into first and second portions of radiation and to recombine the first and second portions of reflected radiation to provide the recombined radiation. The fixed mirror is mounted to the stationary base and configured to reflect the first portion of radiation to provide the first portion of reflected radiation to the beam splitter. The movable mirror is configured to reflect the second portion of radiation to provide the second portion of reflected radiation to the beam splitter, the movable mirror being movable with respect to the beam splitter in a scan direction to change the phase of the second portion of reflected radiation relative to the first portion of reflected radiation. The upper scan carriage is mounted to the stationary base via a pair of inner bearing flexures and is movable in a first arc motion with respect to the stationary base, the beam splitter assembly, the fixed mirror and the movable mirror being positioned within a space between planes containing the pair of inner bearing flexures while in respective unflexed positions. The lower scan carriage is mounted to the upper scan carriage via a pair of outer bearing flexures and movable in a second arc motion with respect to the upper scan carriage, the second arc motion being substantially equal to the first arc motion, while arcing in an opposite direction. The movable mirror is attached to the lower scan carriage such that movement of the upper scan carriage in the first arc motion and movement of the lower scan carriage in the second arc motion enable movement of the movable mirror in the scan direction.

According to another representative embodiment, an interferometer of a Fourier transform infrared spectroscopy system includes a fixed assembly, a movable assembly, a pair of inner bearing flexures, and a pair of outer bearing flexures. The fixed assembly includes a base, a beam splitter configured to split light emitted from a light source into first and second portions of light, and a fixed mirror for reflecting the first portion of light. The movable assembly, which is movable with respect to the fixed assembly, includes an upper scan carriage, a lower scan carriage and a movable mirror connected to the lower scan carriage for reflecting the second portion of light. The beam splitter is further configured to combine the reflected first and second portions of light into a recombined radiation beam. The pair of inner bearing flexures has upper ends connected to the base and lower ends connected to the upper scan carriage, enabling movement of the upper scan carriage relative to the base. The pair of outer bearing flexures has upper ends connected to the upper scan carriage and lower ends connected to the lower scan carriage, enabling movement of the lower scan carriage relative to the upper scan carriage. An upper point in an upper plane of the upper scan carriage defines an upper arc during the movement of the upper scan carriage, and a lower point in a lower plane of the lower scan carriage defines a lower arc, equal and opposite to the upper arc, during the movement of the lower scan carriage, where the upper point and the lower point are geometric conjugates, enabling a scan movement of the movable mirror such that a plane containing the movable mirror is maintained parallel to a plurality of planes containing the movable mirror at a corresponding plurality of distances between the movable assembly and the fixed assembly during the scan movement.

BRIEF DESCRIPTION OF THE DRAWINGS

The illustrative embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1:
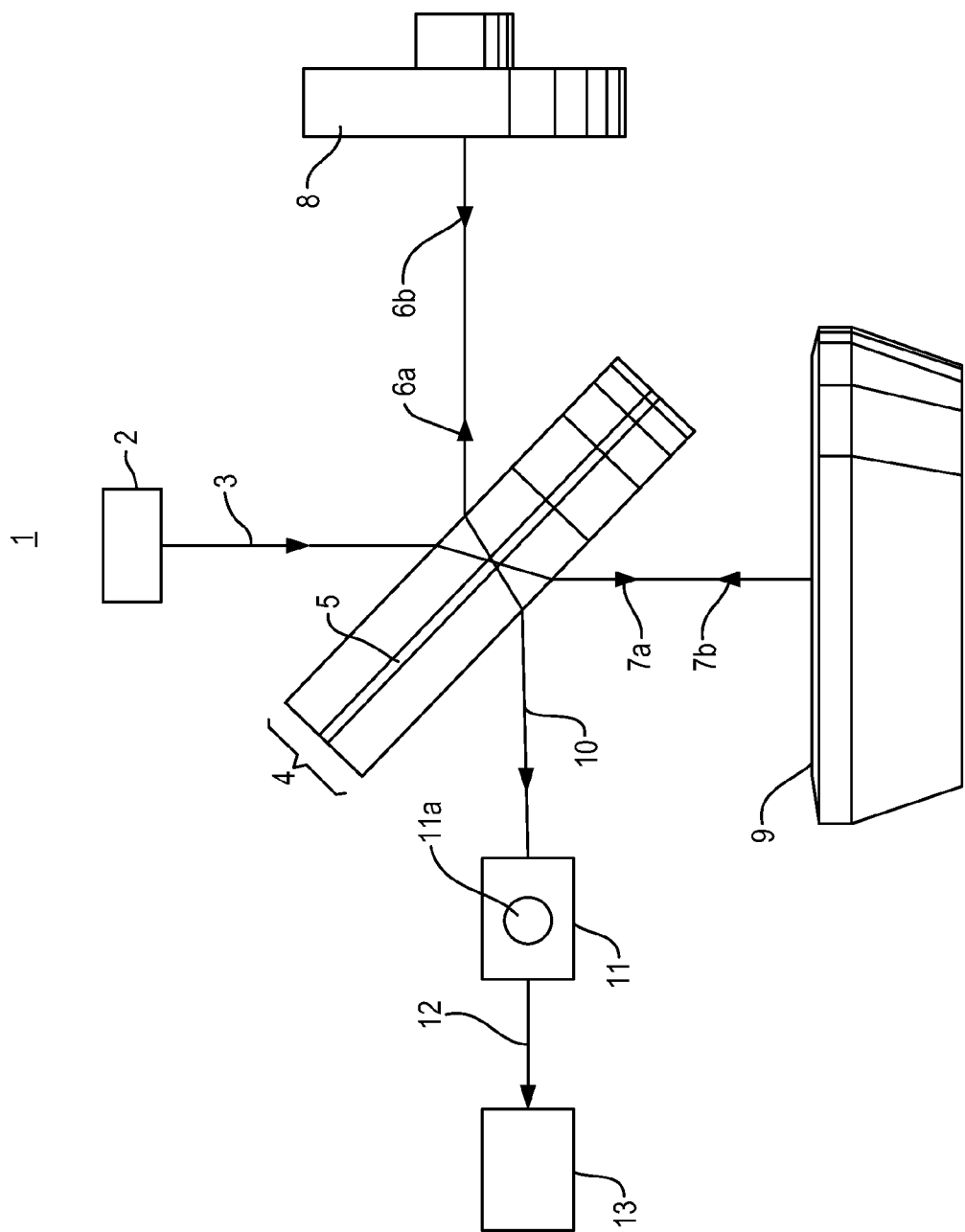
FIG. 1 illustrates a simplified cross-sectional side elevation view of optical elements in an interferometer, according to a representative embodiment.

In the following detailed description, for purposes of explanation and not limitation, illustrative embodiments disclosing specific details are set forth in order to provide a thorough understanding of embodiments according to the present teachings. However, it will be apparent to one having had the benefit of the present disclosure that other embodiments according to the present teachings that depart from the specific details disclosed herein remain within the scope of the appended claims. Moreover, descriptions of well-known devices and methods may be omitted so as not to obscure the description of the example embodiments. Such methods and devices are within the scope of the present teachings.

Generally, it is understood that the drawings and the various elements depicted therein are not drawn to scale. Further, relative terms, such as "above," "below," "top," "bottom," "upper," "lower," "left," "right," "vertical" and "horizontal," are used to describe the various elements' relationships to one another, as illustrated in the accompanying drawings. It is understood that these relative terms are intended to encompass different orientations of the device and/or elements in addition to the orientation depicted in the drawings. For example, if the device were inverted with respect to the view in the drawings, an element described as "above" another element, for example, would now be "below" that element. Likewise, if the device were rotated 90 degrees with respect to the view in the drawings, an element described as "vertical," for example, would now be "horizontal."

FIG. 1 illustrates a simplified cross-sectional side view of optical elements in an interferometer, according to a representative embodiment.

Referring to FIG. 1, optical elements, including a beam splitter 4, a movable mirror 8, and a fixed mirror 9, in an interferometer 1 are illustrated according to a representative embodiment. Light 3 from a light source 2 is directed to the beam splitter 4, which includes a beam splitting surface 5. The light 3 may be infrared radiation and the light source 2 may be a source of infrared radiation, for example. In an embodiment, the interferometer may be used for Fourier transform infrared (FTIR) spectroscopy, for example. The light 3 is split by the beam splitting surface 5 into a transmitted portion 7a (first portion) and a reflected portion 6a (second portion). The reflected portion 6a continues on to the movable mirror 8, which reflects the reflected portion 6a back onto itself as a reflected beam 6b (reflected second portion) that returns to the beam splitting surface 5. In a similar fashion, the transmitted portion 7a continues on to the fixed mirror 9, which reflects the transmitted portion 7a back onto itself as a reflected beam 7b (reflected first portion) that returns to beam splitting surface 5. The reflected beams 6b, 7b are recombined at the beam splitting surface 5 and at least a portion of the reflected beams 6b, 7b is reflected as a recombined radiation beam 10. The recombined radiation beam 10 then continues on to a sampling apparatus 11. The sampling apparatus 11 modifies the recombined radiation beam 10 into sample encoded radiation 12 as a function of a sample 11a in the sampling apparatus 11. The sample encoded radiation 12 continues on to a detection system 13. The sample 11 a is identified as a function of the sample encoded radiation 12. It is understood that changing the location of the light source 2 with the sampling apparatus 11 and the detection system 13 is known to those in the art.

When the respective optical distances from the beam splitting surface 5 to the movable mirror 8 and the fixed mirror 9 are substantially equal, the recombined radiation beam 10 remains in phase, as there is no optical retardation. When the movable mirror 8 moves either closer to or further from the beam splitting surface 5, while a planar surface of the movable mirror 8 maintains angular orientation to the reflected portion 6a, the reflection of the reflected beam 6b returns to beam splitting surface 5 and a retardation change is created. The retardation change in the reflected beam 6b modulates the recombined radiation beam 10.

Figure 2:
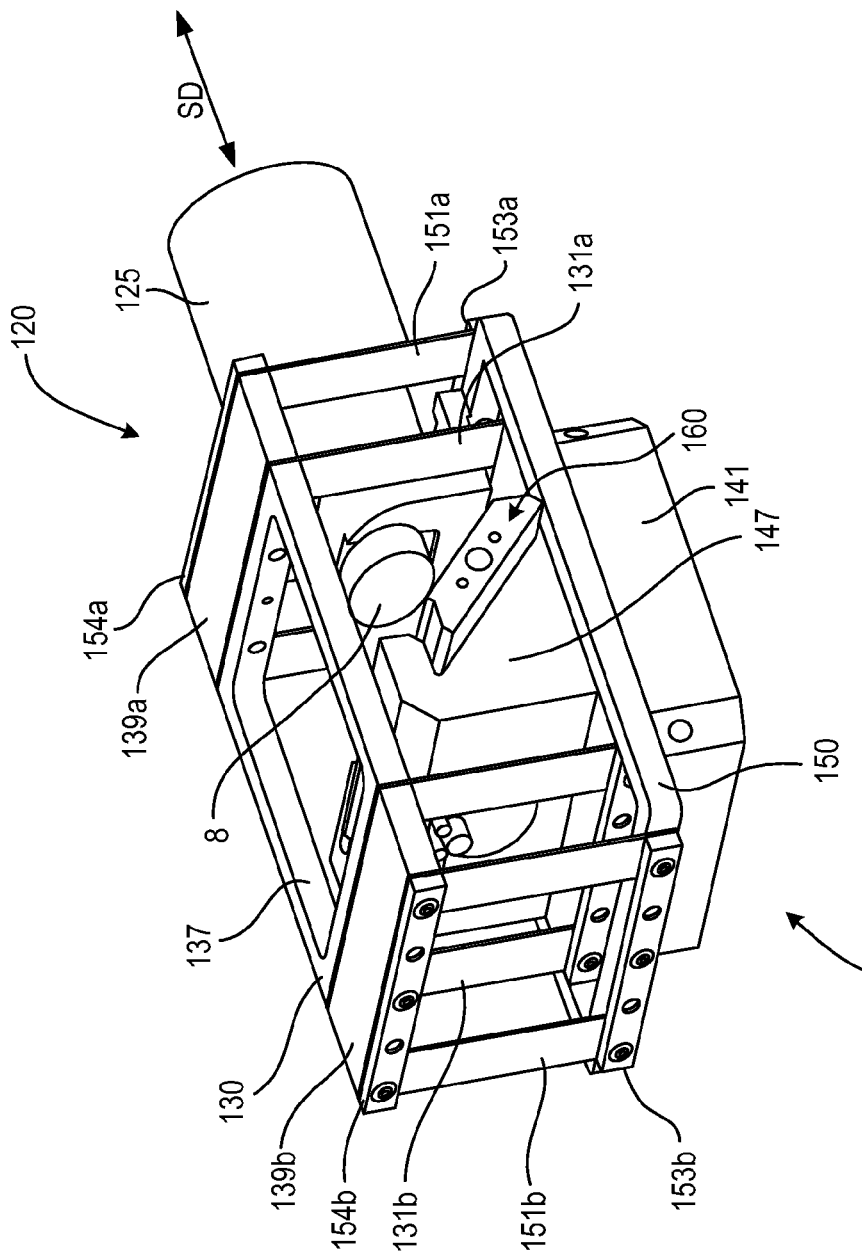
FIG. 2 illustrates a side isometric view of an interferometer, according to a representative embodiment.

When using the interferometer 1 as part of a rapid scanning FTIR system, as shown in FIG. 2, for example, the movable mirror 8 is typically driven at a constant velocity so as to modulate the recombined radiation beam 10 in a known manner that may subsequently be Fourier transformed to recover frequency information of the recombined radiation beam 10 and/or the sample encoded radiation 12. If one or more of the optical elements including the beam splitter 4, the movable mirror 8, and/or the fixed mirror 9 change(s) position(s), or if the optical relationships change between the beam splitter 4, the movable mirror 8, and/or the fixed mirror 9, some amount of modulation change occurs in the recombined radiation beam 10. Such unintended changes in modulation produce unwanted effects and, therefore, are undesirable.

FIG. 2 illustrates a side isometric view of an interferometer, according to a representative embodiment.

Referring to FIG. 2, interferometer 101, which may be used for Fourier transform infrared spectroscopy, for example, includes fixed assembly 140 and movable assembly 120, where the movable mirror 8 and a motor coil assembly 125 are attached to the movable assembly 120. The fixed assembly 140 includes fixed housing or base 141 and a beam splitter support 147, which is integrally combined with the base 141. The beam splitter support 147 provides a guide for movable beam splitter assembly 160 that includes selectable beam splitters 4a, 4b (not shown in FIG. 2), each of which is configured to split the light 3 emitted from the light source 2 into reflected portion 6a and transmitted portion 7a, as discussed above with reference to the beam splitter 4. The base 141 further includes the fixed mirror 9 for reflecting the transmitted portion 7a to provide the reflected beam 7b. The movable assembly 120 is movable with respect to the fixed assembly 140, and includes an upper scan carriage 130 and a lower scan carriage 150. In an embodiment, the movable mirror 8 is connected to the lower scan carriage 150 for reflecting the reflected portion 6a to provide the reflected beam 6b. The beam splitter assembly 160 is configured to combine the reflected beams 6b, 7b into recombined radiation beam 10 which is output to the sampling apparatus 11 and the detection system 13, as discussed above.

The interferometer 101 further includes a pair of inner bearing flexures 131a, 131b (e.g., first inner bearing flexure 131a and second inner bearing flexure 131b) and a pair of outer bearing flexures 151a, 151b (e.g., first outer bearing flexure 151a and second outer bearing flexure 151b). Each of the inner bearing flexures 131a, 131b has a lower end connected to the base 141 and an upper end connected to the upper scan carriage 130, enabling movement (oscillation) of the upper scan carriage 130 relative to the base with minimal scan friction in the plus/minus scan direction SD. Each of the outer bearing flexures 151a, 151b has an upper end connected to the upper scan carriage 130 and a lower end connected to the lower scan carriage 150, enabling movement (oscillation) of the lower scan carriage 150 relative to the upper scan carriage 130 with minimal scan friction in the plus/minus scan direction SD.

The inner bearing flexures 131a, 131b and the outer bearing flexures 151a, 151b may be flat springs, for example, configured to flex or bend substantially to facilitate movement in a scan direction SD of the movable mirror 8. That is, the movement of the upper scan carriage 130 and the movement of the lower scan carriage 150 enable a scan movement of the movable mirror 8 in the scan direction SD when an electromagnetic force is exerted on the motor coil assembly 125. The electromagnetic force is largely exerted either to the left or to the right, as illustrated by the scan direction SD, depending on the polarity of the voltage exerted on the motor coil assembly 125, for example. The motor coil assembly 125 may include a combination of a coil and magnet comprising a linear drive motor operating under servo control that imparts an alternating drive force to the lower scan carriage 150, for example. In the depicted embodiment, as the lower scan carriage 150 moves under motor drive force of the motor coil assembly 125, the outer bearing flexures 151a, 151b bend, thus imparting force into the inner bearing flexures 131a, 131b, which also bend. With each incremental movement of the lower scan carriage 150, this process continues until the requisite travel distance of the movable mirror 8 is achieved in one direction. The polarity of the motor coil assembly 125 may then be reversed, causing a directional change until the requisite travel distance of the movable mirror 8 in the opposite direction is achieved.

The scan movement is restricted such that it maintains a plane containing a reflecting surface of the movable mirror 8 parallel to planes containing the movable mirror 8 of the movable assembly 120 at all respective distances between the movable assembly 120 and the fixed assembly 140 during a scan operation. In other words, because of the restricted movement provided by the inner bearing flexures 131a, 131b and the outer bearing flexures 151a, 151b, the optical relationship between the beam splitter 4a or 4b and the movable mirror 8 remains substantially unchanged except for the optical retardation. Thus, the reflecting surface of the movable mirror 8 does not deflect angularly as the movable assembly 120 is translated relative to the fixed assembly 140. In an embodiment, the movable mirror 8, the fixed mirror 9 and the beam splitter assembly 160 are positioned entirely in a space between planes containing the pair of inner bearing flexures 131a, 131b while in respective flat conditions (unflexed or neutral positions), as shown.

The depicted embodiment using two pairs of bearing flexures, e.g., inner bearing flexures 131a, 131b and outer bearing flexures 151a, 151b, may achieve longer movement distances appropriate for high resolution spectroscopy for example, as compared to the shorter distances appropriate for lower resolution spectroscopy of conventional interferometers using a pair of bearing flexures. The relationship between resolution and requisite scan distance is $L=1/[2(\text{resolution})]$. Specifically, the distance a mechanical bearing must travel for 2 wavenumber resolution is about ±0.25 cm, whereas for ½ wavenumber resolution the travel is about ±1 cm. In other words, this improvement in resolution requires a 4× increase in bearing travel distance, which is achieved using the dual pairs of inner bearing flexures 131a, 131b and outer bearing flexures 151a, 151b as in the depicted embodiment, while maintaining requisite scan parameters and interferometer design goals.

Figure 3:
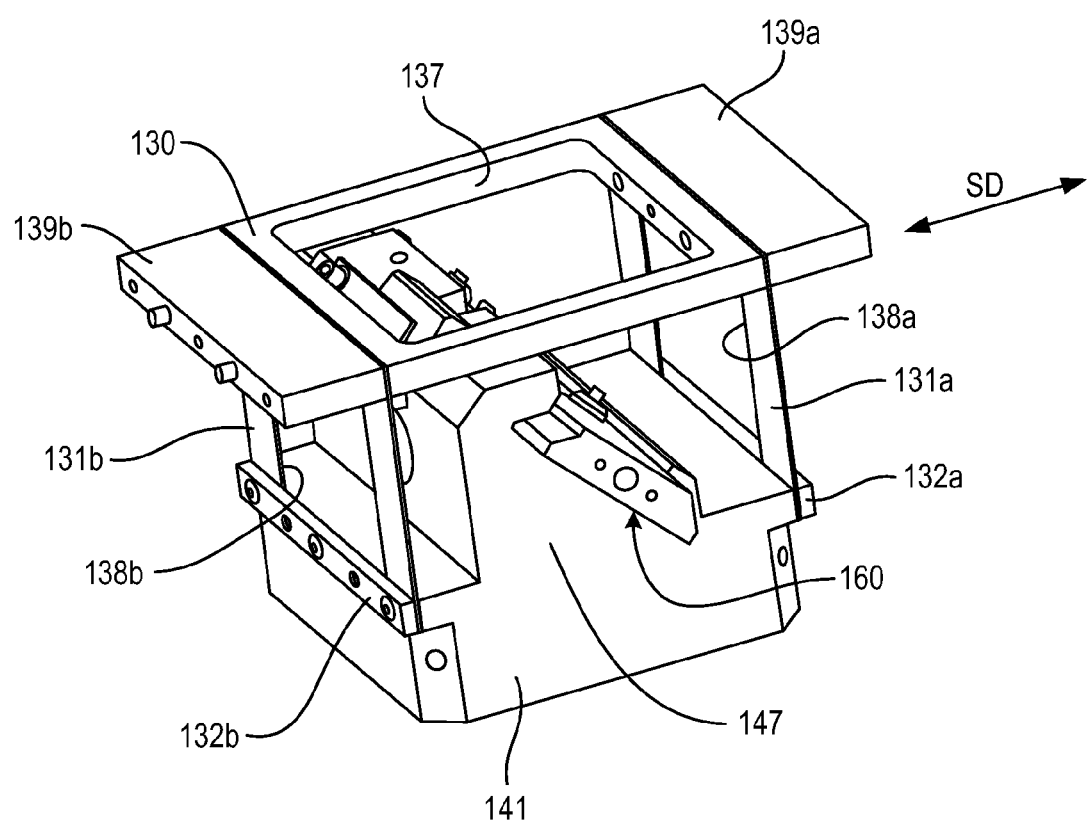
FIG. 3 illustrates a side isometric view of the upper scan carriage and base of an interferometer, according to a representative embodiment.
Figure 4:
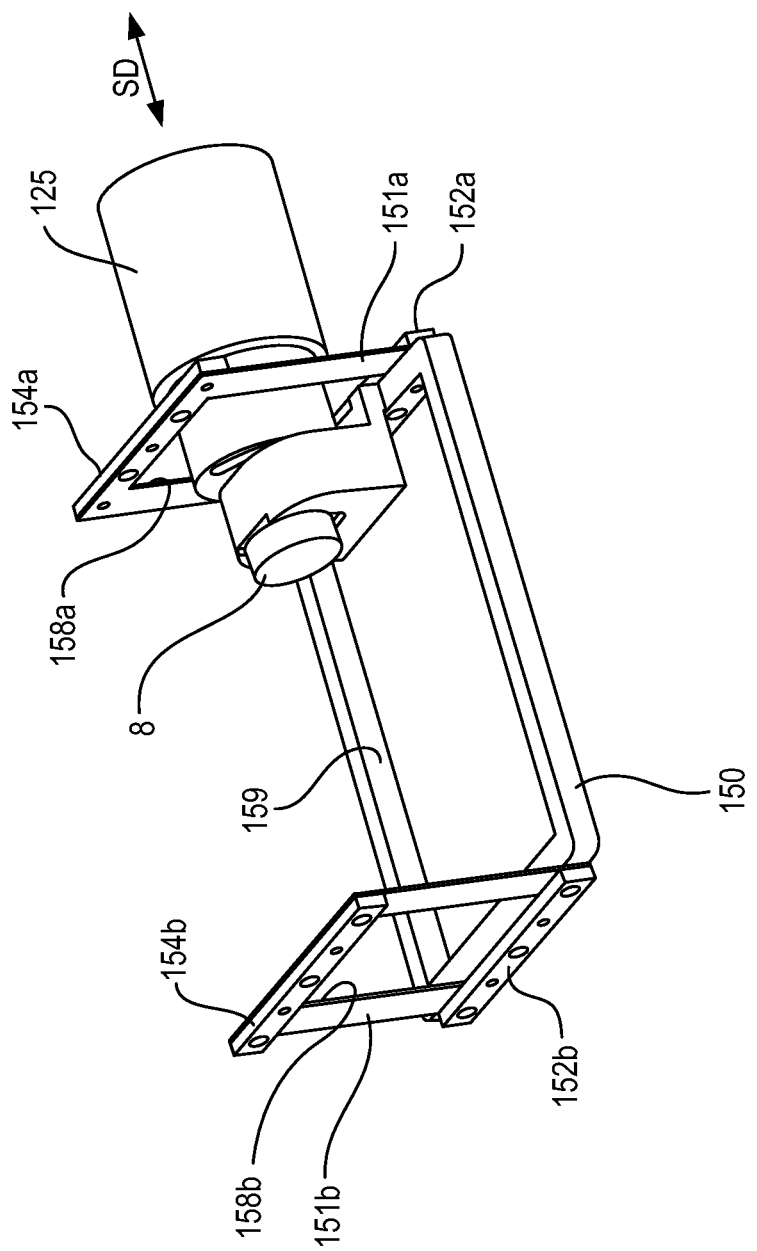
FIG. 4 illustrates a side isometric view of the lower scan carriage of an interferometer, according to a representative embodiment.

FIGS. 3 and 4 illustrate side isometric views of the upper scan carriage 130 (connected to the base 140) and the lower scan carriage 150, according to a representative embodiment.

The upper scan carriage 130 is shown attached to the inner bearing flexures 131a, 131b, which are also attached to the base 141 of the fixed assembly 140. The base 141 supports the beam splitter assembly 160, discussed below. The upper scan carriage 130 defines an upper opening 137 through which the light 3 is able to pass to impinge on one of the selectable beam splitters 4a, 4b. The inner bearing flexure 131a (also shown in FIG. 5) defines an opening 138a through which the movable mirror 8 and at least a portion of the motor coil assembly 125 may be inserted, and the opposing inner bearing flexure 131b defines an opening 138b which provides an unobstructed optical path of the recombined radiation beam 10 from the beam splitter assembly 160.

The lower scan carriage 150 is shown attached to the outer bearing flexures 151a, 151b. The movable mirror 8 and the motor coil assembly 125 are attached to the lower scan carriage 150. The lower scan carriage 150 defines a lower opening 159 in which the base 141 of the fixed assembly 140 may be positioned with sufficient clearance to enable the lower scan carriage 150 to move freely in relation to the base 141 when the upper ends of the outer bearing flexures 151a, 151b are attached to the lower scan carriage 150, as shown in FIG. 2, discussed above. The outer bearing flexure 151a defines an opening 158a providing clearance through which the movable mirror 8 and at least a portion of the motor coil assembly 125 may be inserted, and the opposing outer bearing flexure 151b defines an opening 158b through which the recombined radiation beam 10 may be transmitted unrestricted. The openings 138a, 138b may be substantially aligned with the openings 151a, 151b, respectively.

Figure 5:
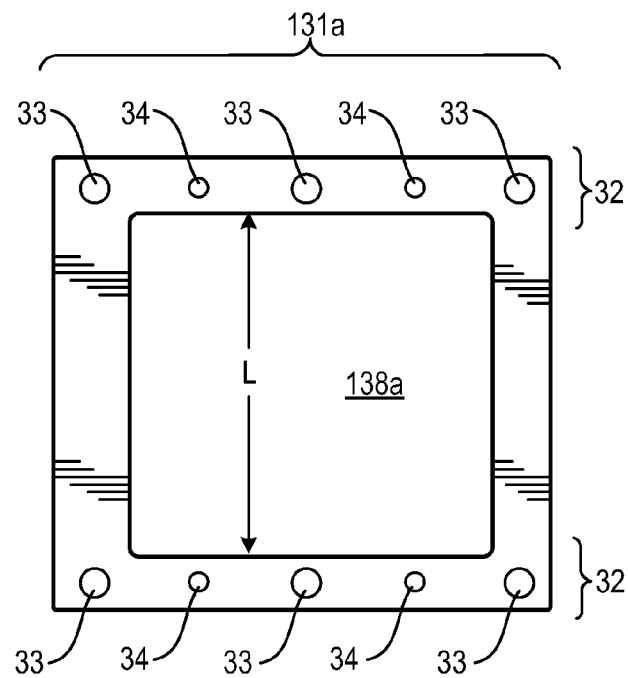
FIG. 5 illustrates a front elevation view of a bearing flexure in an interferometer, according to a representative embodiment.

FIG. 5 illustrates a front elevation view of an example of a bearing flexure in an interferometer, according to a representative embodiment. The bearing flexure shown in FIG. 5 is identified as the inner bearing flexure 131a, although it is understood that the bearing flexure is representative of any of the inner bearing flexures 131a, 131b and/or the outer bearing flexures 158a, 158b. Generally, the inner bearing flexures 131a, 131b are substantially the same size and shape as one another, and the outer bearing flexures 151a, 151b are likewise substantially the same size and shape as one another. Further, the pair of inner bearing flexures 131a, 131b may be substantially the same size and shape as the pair of outer bearing flexures 151a, 151b, as shown.

The representative inner bearing flexure 131a includes the opening 138a, which may be substantially rectangular in shape. The opening 138a provides appropriate modulus characteristics for both bearing the weight of the movable assembly 120 and providing resistance to undesirable shocks, torques, and shears imposed by environmental forces. Although the opening 138a is rectangular in the illustrated embodiment, it is understood that other embodiments may include other shapes for the opening 138a of the inner bearing flexure 131a (as well as the openings 138b, 158a, 158b), such as oblong, elliptical, circular, or any other shape that might improve robustness and/or stability, without departing from the scope of the present teachings.

Figure 6:
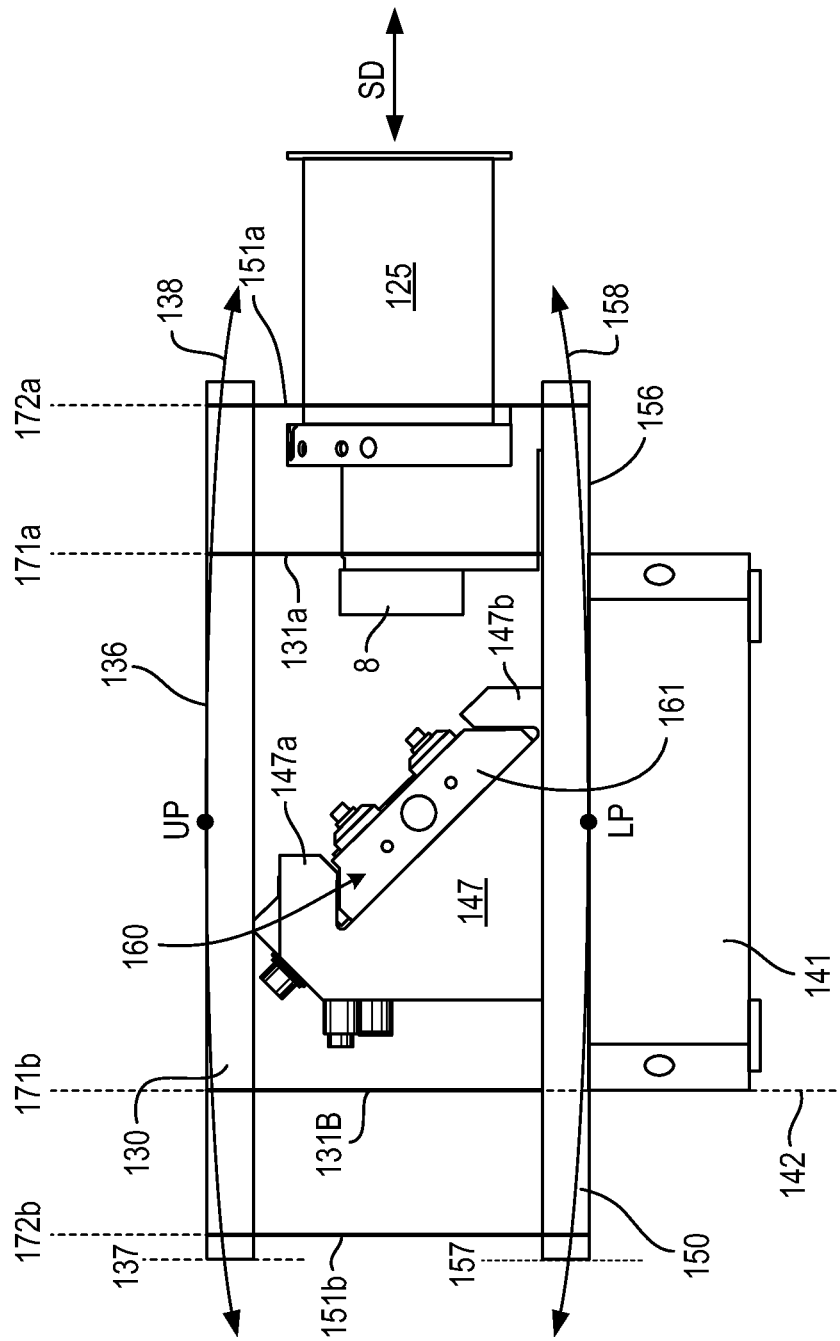
FIG. 6 illustrates a side elevation view of an interferometer, according to a representative embodiment.

FIG. 6 illustrates a side elevation view of an interferometer, in an assembled state, according to a representative embodiment.

Referring to FIG. 6, the interferometer 101 includes the fixed assembly 140 and the movable assembly 120, where the movable mirror 8 and the motor coil assembly 125 are attached to the movable assembly 120. The fixed assembly 140 includes the base 141 and the beam splitter support 147.

The beam splitter support 147 includes upper flange 147a and lower flange 147b confined to secure the movable beam splitter assembly 160, and guide movement of the beam splitter assembly 160, as discussed below. The movable assembly 120 is movable with respect to the fixed assembly 140, and includes the upper scan carriage 130 and the lower scan carriage 150. The inner bearing flexures 131a, 131b are connected to the upper scan carriage 130 and the base 141, and the outer bearing flexures 151a, 151b are connected to the upper scan carriage 130 and the lower scan carriage 150. In an embodiment, the movable mirror 8 is connected to the lower scan carriage 150 for reflecting the reflected portion 6a to provide the reflected beam 6b.

As discussed above, the movable mirror 8 moves in the scan direction SD through operation of the motor coil assembly 125. The upper scan carriage 130 and the lower scan carriage 150 move together in a manner that maintains the plane of the movable mirror 8 parallel to all planes containing the movable mirror 8 along the scan path moving in the scan direction SD (left or right, in the depicted orientation). More particularly, the upper scan carriage 130 includes an upper plane 136 and the lower scan carriage 150 includes a lower plane 156, where the upper plane 136 and the lower plane 156 are substantially parallel to one another when the inner bearing flexures 131a, 131b and the outer bearing flexures 151a, 151b are in the neutral or unflexed positions. The upper plane 136 and the lower plane 156 are also substantially parallel to the scan direction SD when the inner bearing flexures 131a, 131b and the outer bearing flexures 151a, 151b are in the neutral or unflexed positions. Thus, when the movable mirror 8 moves (left or right) in the scan direction SD, an upper point UP in the upper plane 136 of the upper scan carriage 130 defines an upper arc 138 in the same general direction (left or right) as the movable mirror 8, while a lower point LP in the lower plane 156 of the lower scan carriage 150 defines a lower arc 158 in the same general direction (left or right) as the movable mirror 8. In an embodiment, the lower arc 158 is substantially equal and opposite to the upper arc 138 when the lower point LP and the upper point UP are geometric conjugates of each other. The upper point UP follows the upper arc 138 and the lower point follows the lower arc 158 in response to the simultaneous flexing or bending of the inner bearing flexures 131a, 131b and the outer bearing flexures 151a, 151b.

In addition, the inner bearing flexures 131a, 131b define inner planes 171a, 171b, respectively, in the neutral or unflexed position, and the outer bearing flexures 151a, 151b define outer planes 172a, 172b, respectively, in the neutral or unflexed position. In an embodiment, the inner planes 171a, 171b and the outer planes 172a, 172b are substantially parallel to one another. Further, the upper scan carriage 130 contains a front plane 137 that is substantially parallel to the inner planes 171a, 171b of the inner bearing flexures 131a, 131b in the neutral or unflexed position. The front plane 137 is also substantially parallel to a front plane 142 of the base 141 when the inner bearing flexures 131a, 131b are in the neutral or unflexed position. Similarly, the lower scan carriage 150 contains a front plane 157 that is substantially parallel to outer planes 172a, 172b of the outer bearing flexures 151a, 151b in the neutral or unflexed position. The front plane 157 is also substantially parallel to the front plane 137 when the inner bearing flexures 131a, 131b and the outer bearing flexures 151a, 151b are in the neutral or unflexed positions. In an embodiment, the front plane 137 of the upper scan carriage 130 remains parallel to the front plane 142 of the base 141 throughout the scan movement, and the front plane 157 of the lower scan carriage 150 remains parallel to the front plane 137 of the upper scan carriage 130 (as well as the front plane 142 of the base 141) throughout the scan movement.

Figure 7:
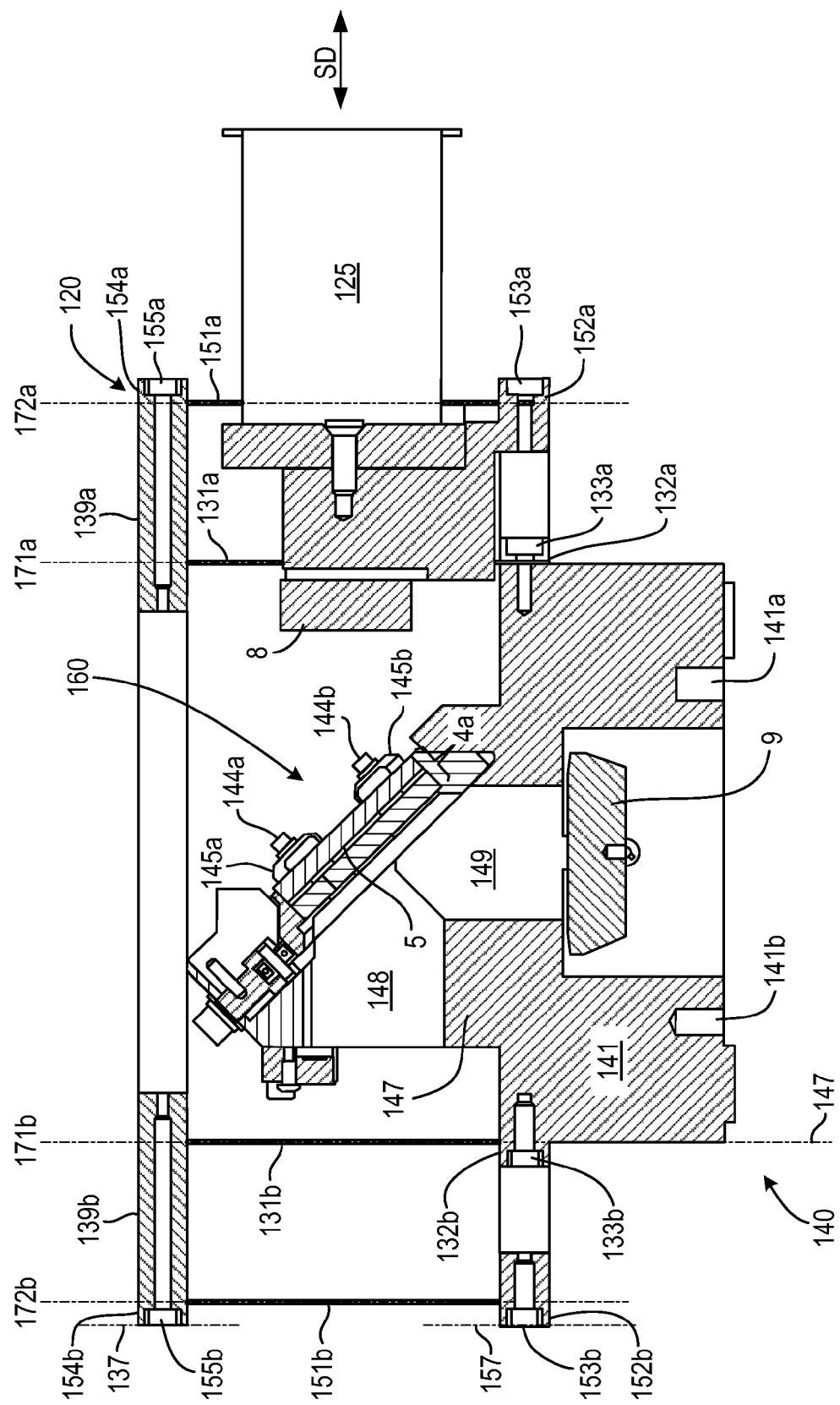
FIG. 7 illustrates a cross-section side elevation view of an interferometer, according to a representative embodiment.

FIG. 7 illustrates a cross-section side view of an interferometer, according to a representative embodiment.

Referring to FIG. 7, the interferometer 101 includes the fixed assembly 140 and the movable assembly 120. The fixed assembly 140 includes the fixed mirror 9 and the beam splitter assembly 160, as well as various affixing means. In the depicted illustrative configuration, the affixing means include inner clamp members 132a, 132b and corresponding fasteners 133a, 133b (e.g., screws) for attaching lower ends of the inner bearing flexures 131a, 131b to the base 141. Multiple threaded holes 141a, 141b may be provided in the base 141 for affixing the interferometer 101 to a frame, instrument housing, or base plate (not shown), for example.

The beam splitter assembly 160 includes a beam splitter 4a and a beam splitter 4b (not shown in FIG. 7) on a beam splitter carriage 161 slidably mounted to the beam splitter support 147 of the fixed assembly 140 to enable selection of one of multiple selectable beam splitters 4a and 4b by sliding one of the beam splitters 4a, 4b into a path of the light 3 emitted from the light source 2, as discussed below with reference to FIGS. 7 and 9. The beam splitter 4a is mounted to a surface of the beam splitter carriage 161 by beam splitter fasteners 144a, 144b and corresponding 0-rings 145a, 145b. Opening 148 in the beam splitter support 147 provides clearance for the recombined radiation beam 10 output to the sampling apparatus 11 and the detection system 13, and opening 149 in the beam splitter support 147 and the base 141 provides clearance for the transmitted portion 7a transmitted to the fixed mirror 9 and the reflected beam 7b reflected from the fixed mirror 9. The light 3 from the light source 2 enters the fixed assembly 140 of the interferometer 101 via the upper opening 137, defined by the upper scan carriage 130, to reach the beam splitter 4a.

The movable assembly 120 includes the upper scan carriage 130, the lower scan carriage 150, the movable mirror 8, and the motor coil assembly 125, as well as various affixing means. In an embodiment, the movable mirror 8 and the motor coil assembly 125 are connected to the lower scan carriage 150, and the movable mirror 8 is configured to reflect the reflected portion 6a back onto itself as the reflected beam 6b. Alternatively, the movable mirror 8 and the motor coil assembly 125 may be connected to the upper scan carriage 130, and the lower scan carriage 150 connected to the base 140, without departing from the scope of the present teachings.

In the depicted illustrative configuration, the affixing means of the movable assembly 120 include outer clamp members 152a, 152b and corresponding fasteners 153a, 153b (e.g., screws) for attaching lower ends of the outer bearing flexures 151a, 151b to the lower scan carriage 150. The affixing means of the movable assembly 120 further include inner clamp members 139a, 139b, outer clamp members 154a, 154b, and corresponding fasteners 155a, 155b (e.g., screws) for attaching upper ends of the inner bearing flexures 131a, 131b and upper ends of the outer bearing flexures 151a, 151b to the upper scan carriage 130, respectively. All components of the movable assembly 120 are rigidly fastened to form a unit that moves together when actuated by an electromagnetic force exerted on the motor coil assembly 125 in the scan direction SD, as discussed above. The use of motor coils for driving movable mirrors of interferometers to achieve retardation (e.g., distance) between the fixed and movable assemblies 140, 120, respectively, is known.

Generally, the inner clamp members 132a, 132b and the fasteners 133a, 133b act as means to affix the inner bearing flexures 131a, 131b to the base 141. Movement between the movable and fixed assemblies 120, 140 occurs as the inner bearing flexures 131a, 131b and the outer bearing flexures 151a, 151b deflect with relative motion of the upper scan carriage 130. Likewise, the outer clamp members 152a, 152b and fasteners 153a, 153b act as means to affix the outer bearing flexures 151a, 151b to the lower scan carriage 150, and the inner clamp members 139a, 139b, the outer clamp members 154a, 154b, and the fasteners 155a, 155b act as means to affix the inner bearing flexures 131a, 131b and the outer bearing flexures 151a, 151b to the upper scan carriage 130, while allowing movement between the movable and fixed assemblies 120, 140. In alternative embodiments, adhesives, braise solder, welding, epoxy, and extruded metal may be used to affix the inner/outer bearing flexures to the movable and fixed assemblies 120, 140.

The optical relationship between the beam splitter 4a, 4b and the movable mirror 8 may be satisfied when an angle of a surface of the beam splitter 4a, 4b is maintained relative to an angle of a surface of the movable mirror 8. Similarly, the optical relationship between the beam splitter 4a, 4b and the movable mirror 8 may be satisfied when an angle of an axis of a beam, from the beam splitter 4a, 4b toward the movable mirror 8 is maintained at a predetermined angle relative to the surface of the movable mirror 8.

As discussed above, the beam splitter assembly 160, the fixed mirror 9, and the movable mirror 8 are positioned in the space between inner planes 171a, 171b containing the inner bearing flexures 131a, 131b, respectively, in their flat condition.

Referring again to FIG. 5, in the illustrated embodiment, the clamped areas 32 of the representative inner bearing flexure 131a further align with the edges of the clamp members 132a, 139a to define unrestricted clamping length L. Clearance holes 33 are provided for the fasteners 133a, 155a, and alignment holes 34 are provided to accommodate high tolerance pins (not shown) for precise positioning. Similarly, the clamped areas 32 and clearance holes 33 of the inner bearing flexure 131b would align with the edges of the clamp members 132b, 139b, and receive the fasteners 133b, 155b. Also, the clamped areas 32 and clearance holes 33 of the outer bearing flexures 151a, 151b would align with the edges of the clamp members 152a, 152b, 154a, 154b, and receive the fasteners 153a, 153b, 155a, 155b, respectively.

Figure 8:
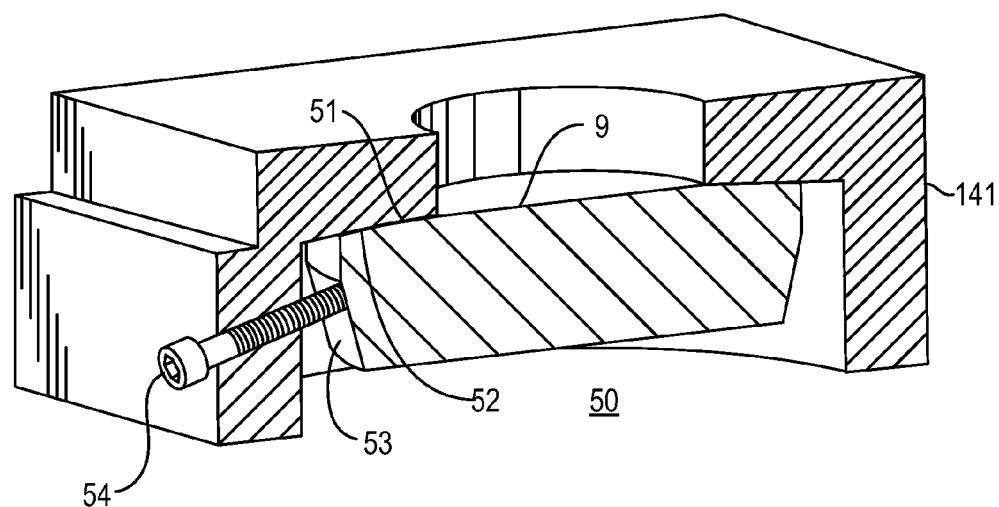
FIG. 8 illustrates an isometric cross-sectional view showing detail of a fixed mirror and mechanism for moving it relative to a fixed assembly, according to a representative embodiment.

FIG. 8 illustrates an isometric cross-sectional view showing detail of a fixed mirror and mechanism for moving it relative to a fixed assembly, according to a representative embodiment.

Referring to FIG. 8, the fixed mirror 9 is positioned in a fixed mirror cavity 50. More specifically, a spherical surface portion 51 of the base 141 contacts a spherical surface portion 52 of the fixed mirror 9. Six (6) adjustment screws, one of which is illustrated as 54, contact a conical surface 53 of the fixed mirror 9. In an embodiment, the screws 54 are placed approximately symmetrically around a circumference of the conical surface 53. In this manner, the screws 54 may be used to adjust the orientation of the fixed mirror 9. The fixed mirror adjustment may be operated with servo or stepper motors (not shown), for example, although other means of adjusting the fixed mirror 9 may be incorporated without departing from the scope of the present teachings.

Figure 9:
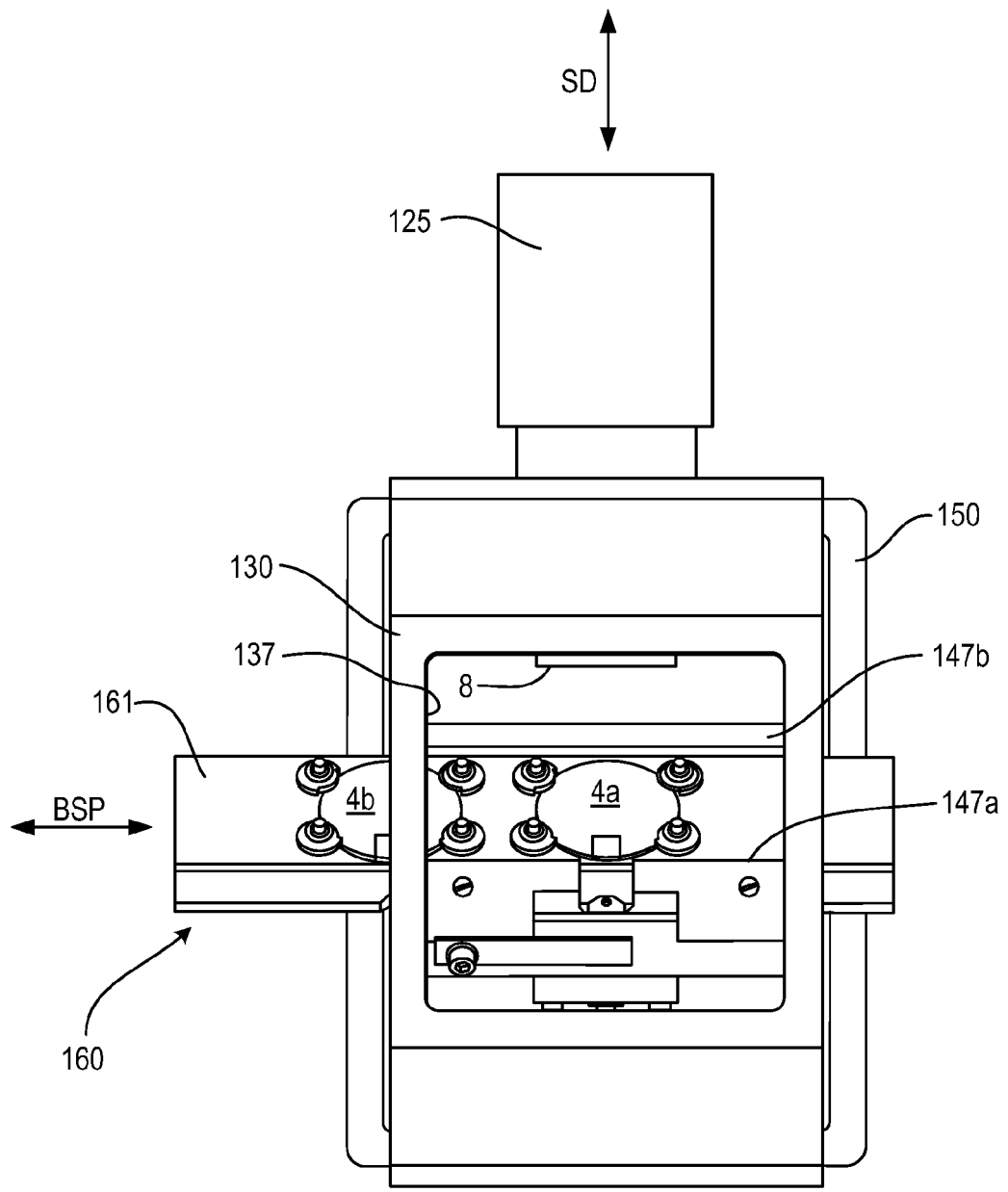
FIG. 9 illustrates a top plan view of a movable beam splitter assembly of an interferometer, according to a representative embodiment.

FIG. 9 illustrates a top plan view of a movable beam splitter assembly of an interferometer, according to a representative embodiment.

Referring to FIG. 9, the beam splitter assembly 160 includes the beam splitter carriage 161, which is slidably mounted to the beam splitter support 147 and/or the stationary base 141. Multiple beam splitters 4a, 4b are positioned adjacent to one another on an upper surface of the beam splitter carriage 161. The beam splitter carriage 161 is configured to slide within the flanges 147a, 147b of the beam splitter support 147 in a beam splitter positioning direction BSP, which is substantially perpendicular to the scan direction SD. Thus, the sliding operation of the beam splitter carriage 161 selectively places one of the beam splitters 4a, 4b into the path of the light 3 emitted from the light source 2 (not shown in FIG. 9). The beam splitter carriage 161 may be operated using a servo or stepper motor (not shown), for example, although other means of sliding the beam splitter carriage 161 may be incorporated without departing from the scope of the present teachings.

In the depicted arrangement, the beam splitter carriage 161 has been positioned to select the beam splitter 4a. The beam splitters 4a, 4b may be formed of different materials to transmit different frequencies of interest of the light 3 emitted from the light source 2, respectively. For example, the beam splitters 4a, 4b may be configured with various combinations of ZnSe, KBr, or CaF2. Although FIG. 9 depicts the two beam splitters 4a, 4b, it is understood that the beam splitter carriage 161 may include additional beam splitters without departing from the scope of the present teachings. It is further understood that various embodiments of the interferometer 101 may be implemented using a single, fixed beam splitter as opposed to selectable beam splitters.

During use, the two primary sources of optical misalignment and instability are strains from mechanical and thermal stresses on the interferometer 101. In an embodiment, the inner bearing flexures 131a, 131b and the outer bearing flexures 151a, 151b are manufactured in matched sets or pairs, and assembled to assure substantially precisely repeatable trajectories and relationships between the movable mirror 8 on the movable assembly 120 and the beam splitter 4a, 4b and/or fixed mirror 9 on the fixed assembly 140, which remain precisely fixed relative to each other.

Using the pair of inner bearing flexures 131a, 13 lb and the pair of outer bearing flexures 151a, 151b, where respective inner planes 171a, 171b bound a space that contains the interferometer optical elements (e.g., the beam splitter 4a, 4b, the fixed mirror 9, and the movable mirror 8) provides significant symmetry, minimum optical path lengths for the radiation, and minimum structural lengths. These features, along with proper selection of materials, minimize the effects of thermal changes in the surrounding spaces. The illustrated embodiment further provides a clear optical path for input or output radiation and a mechanical means for conveniently driving the movable assembly 120 including the movable mirror 8. Simultaneously, the symmetry and compactness of the inner bearing flexures 131a, 131b and the outer bearing flexures 151a, 151b minimize strains from thermal and mechanical stresses. Significantly reduced strains result in significantly improved optical stability.

Temperatures change constantly and are typically unpredictable in many instrument operating environments. Interferometers that need to function in such environments typically need to be isolated from the temperature changes, have compensation means to counteract the effects of the changes, and/or minimize the effects of such temperature changes. Historically, interferometers have been designed to be isolated from environmental changes and to counteract the effects of environmental changes. The various embodiments herein help reduce and/or minimize the effects of environmental changes.

In general, dimensions of a substance increase as the temperature of the substance itself increases. This relationship is typically stated according to the following formula: $L=L_o(1+A(t-t_o))$, where $L_o$ is the length of an object at temperature $t_o$, A is a coefficient of linear expansion, and L is the length of the object at temperature t. The coefficient of linear expansion A is known for most common materials. In an infrared interferometer, the selection of the beam splitter material determines the useful frequency range of the instrument.

One commonly used material, Zinc Selenide (ZnSe) has $A=7.2\times10^{-6}/C$. When using a typical one inch diameter (25.4 millimeters) beam splitter, there is approximately 1.5 microns change in diameter for each ten degree change on the centigrade scale if the beam splitter diameter is unrestricted. While this change appears relatively small, it is capable of creating enormous stresses if the beam splitter were constrained. For example, for a ZnSe beam splitter that is securely affixed to an aluminum housing (a common practice for commercial FTIRs), the aluminum would attempt to change at approximately three times the rate of the ZnSe. The resulting stress, if not properly dissipated, could cause surface distortion and/or angular (e.g., tilt) change that may result in modulation change and instability.

In an embodiment, the base 141, the upper scan carriage 130, the lower scan carriage 150, the inner bearing flexures 131a, 131b, the outer bearing flexures 151a, 151b, the clamp members 132a, 132b, 139a, 139b, 152a, 152b, 154a, 154b, the fasteners 133a, 133b, 153a, 153b, 155a, 155b, the movable mirror 8, and the fixed mirror 9 each may be formed of steel, for example. In addition, it is contemplated that the movable mirror 8 and the fixed mirror 9 include a metalized film for improved reflectivity in the infrared range, for example.

Steel and titanium have coefficients of thermal expansion much closer to that of ZnSe. Therefore, using steel or titanium in place of aluminum housing would reduce the strain differential between the ZnSe and the housing. However, the benefit of improving strain differential by changing from aluminum to steel or titanium to overcome other factors such as shape, thermal conductivity, thermal absorption, and thermal emissivity, among others, has not been previously demonstrated. Presumably, the improved strain differential has alone not achieved improved results because other factors have been a source of optical instability. In that regard, the various embodiments described herein suggest that the roles of shape and symmetry are of equal, if not greater, importance than the role of differential coefficients of thermal expansion.

While the disclosure references exemplary embodiments, it will be apparent to those skilled in the art that various changes and modifications may be made without departing from the spirit and scope of the present teachings. Therefore, it should be understood that the above embodiments are not limiting, but illustrative.

What is claimed:

1. An interferometer, comprising:
a first assembly comprising a base, a beam splitter assembly configured to split light emitted from a light source into first and second portions of light, and a fixed mirror for reflecting the first portion of light;
a second assembly, movable with respect to the first assembly, comprising a first scan carriage, a second scan carriage and a movable mirror connected to the second scan carriage for reflecting the second portion of light, wherein the beam splitter assembly is further configured to combine the reflected first and second portions of light into a recombined radiation beam;

a pair of inner bearing flexures having ends connected to the base and ends connected to the first scan carriage, enabling movement of the first scan carriage relative to the base; and a pair of outer bearing flexures having ends connected to the first scan carriage and ends connected to the second scan carriage, enabling movement of the second scan carriage relative to the first scan carriage, wherein the movement of the first scan carriage and the movement of the second scan carriage enable a scan movement of the movable mirror in a scan direction restricted such that the scan movement maintains a plane containing the movable mirror parallel to a plurality of planes containing the movable mirror at respective distances between the second assembly and the first assembly during the scan movement.

2. The interferometer of claim 1, wherein a first point in a first plane of the first scan carriage defines an first arc during the movement of the first scan carriage, and a second point in a second plane of the second scan carriage defines a second arc, equal and opposite to the first arc, during the movement of the second scan carriage, wherein the first point and the second point are geometric conjugates.

3. The interferometer of claim 1, wherein the first scan carriage contains a front plane that is substantially parallel to a plane of the pair of inner bearing flexures in an unflexed position, the front plane of the first scan carriage remaining parallel to a front plane of the base throughout the scan movement.

4. The interferometer of claim 3, wherein the second scan carriage contains a front plane that is substantially parallel to a plane of the pair of outer bearing flexures in an unflexed position, the front plane of the second scan carriage remaining parallel to the front plane of the first scan carriage throughout the scan movement.

5. The interferometer of claim 1, wherein the beam splitter assembly, the fixed mirror and the movable mirror are positioned within a space between the planes containing the pair of inner bearing flexures while in respective flat conditions.

6. The interferometer of claim 5, wherein each of a first inner bearing flexure of the pair of inner bearing flexures and a first outer bearing flexure of the pair of outer bearing flexures defines a first opening for providing a clearance for at least one of the movable mirror and the motor coil assembly.

7. The interferometer of claim 6, wherein a second inner bearing flexure of the pair of inner bearing flexures and a second outer bearing flexure of the pair of outer bearing flexures define a second opening for providing an unobstructed optical path of the recombined radiation beam from the beam splitter assembly.

8. The interferometer of claim 7, wherein a surface of the movable mirror does not deflect angularly as the movable assembly is translated relative to the fixed assembly.

9. The interferometer of claim 1, wherein the beam splitter assembly comprises a plurality of selectable beam splitters.

10. The interferometer of claim 9, wherein the plurality of selectable beam splitters comprise different materials to transmit different frequencies of interest of the light emitted from the light source, respectively.

11. The interferometer of claim 9, wherein the beam splitter assembly further comprises a beam splitter carriage containing the plurality of selectable beam splitters, the beam splitter carriage being mounted to the fixed assembly to enable dynamic selection of one of the plurality of selectable beam splitters by sliding the one of the plurality of selectable beam splitters into a path of the light emitted from the light source.

12. A Fourier transform infrared spectroscopy system, comprising:

a light source configured to emit infrared radiation; and
an interferometer comprising:
a beam splitter assembly mounted to a base and configured to split the infrared radiation emitted from the light source into first and second portions of radiation and to recombine the first and second portions of reflected radiation to provide recombined radiation comprising first and second portions of reflected radiation having varying relative phases;

a fixed mirror mounted to the base and configured to reflect the first portion of radiation to provide the first portion of reflected radiation to the beam splitter;

a movable mirror configured to reflect the second portion of radiation to provide the second portion of reflected radiation to the beam splitter, the movable mirror being movable with respect to the beam splitter in a scan direction to change the phase of the second portion of reflected radiation relative to the first portion of reflected radiation;

a first scan carriage mounted to the base and movable in a first arc motion with respect to the stationary base; and a second scan carriage mounted to the first scan carriage and movable in a second arc motion with respect to the first scan carriage, the second arc motion being substantially equal to the first arc motion, while arcing in an opposite direction, wherein the movable mirror is attached to the second scan carriage such that movement of the first scan carriage in the first arc motion and movement of the second scan carriage in the second arc motion enable movement of the movable mirror in the scan direction.

13. The Fourier transform infrared spectroscopy system of claim 12, wherein the first scan carriage is mounted to the base via inner bearing flexures, and the second scan carriage is mounted to the first scan carriage via outer bearing flexures.

14. The Fourier transform infrared spectroscopy system of claim 13, wherein each inner bearing flexure comprises an end connected to the base and an end connected to the first scan carriage, and wherein each outer bearing flexure comprises an end connected to the first scan carriage and an end connected to the second scan carriage.

15. The Fourier transform infrared spectroscopy system of claim 14, wherein the inner bearing flexures are positioned within the outer bearing flexures, and the fixed mirror and the movable mirror are positioned within a space between the inner bearing flexures when the inner bearing flexures are in an un-flexed position.

16. The Fourier transform infrared spectroscopy system of claim 12, wherein the beam splitter assembly comprises a beam splitter carriage configured to selectively place one of a plurality of beam splitters positioned in the beam splitter carriage into the path of the infrared radiation emitted from the light source.

17. The Fourier transform infrared spectroscopy system of claim 16, wherein the plurality of beam splitters comprise different materials to transmit different frequencies of interest of the infrared radiation emitted from the light source, respectively.

18. The Fourier transform infrared spectroscopy system of claim 13, wherein the first scan carriage contains a front plane that is substantially parallel to a plane of the inner bearing flexures while in respective un-flexed positions and a front plane of the base, the front plane of the first scan carriage remaining parallel to the front plane of the base throughout the movement of the first scan carriage in the first arc motion, and wherein the second scan carriage contains a front plane that is substantially parallel to a plane of the outer bearing flexures while in respective un-flexed positions and the front plane of the first scan carriage, the front plane of second scan carriage remaining parallel to the front plane of the first scan carriage throughout the movement of the second scan carriage in the second arc motion.

19. An interferometer of a Fourier transform infrared spectroscopy system, the interferometer comprising:
   a fixed assembly comprising a base, a beam splitter configured to split light emitted from a light source into first and second portions of light, and a fixed mirror for reflecting the first portion of light; and
   a movable assembly, movable with respect to the fixed assembly, comprising a first scan carriage, a second scan carriage and a movable mirror connected to the second scan carriage for reflecting the second portion of light, wherein the beam splitter is further configured to combine the reflected first and second portions of light into a recombined radiation beam;
   wherein the first scan carriage is movable relative to the base, and the second scan carriage is moveable relative to the first scan carriage, and
   wherein a first point in a first plane of the first scan carriage defines a first arc during the movement of the first scan carriage, and a second point in a second plane of the second scan carriage defines a second arc, equal and opposite to the first arc, during the movement of the second scan carriage, the first point and the second point being geometric conjugates.

20. The interferometer of claim 19, wherein the first and second points being geometric conjugates enables a scan movement of the movable mirror such that a plane containing the movable mirror is maintained parallel to a plurality of planes containing the movable mirror at a corresponding plurality of distances between the movable assembly and the fixed assembly during the scan movement.

* * * * *